US009241770B2

(12) United States Patent
Stokes et al.

(10) Patent No.: US 9,241,770 B2
(45) Date of Patent: Jan. 26, 2016

(54) METHODS AND DEVICES FOR REMOTELY CONTROLLING MOVEMENT OF SURGICAL TOOLS

(75) Inventors: Michael J. Stokes, Cincinnati, OH (US); David N. Plescia, Cincinnati, OH (US); David Stefanchik, Morrow, OH (US); Omar J. Vakharia, Cincinnati, OH (US); Andrew Yoo, Cincinnati, OH (US); James T. Spivey, Cincinnati, OH (US); Christopher J. Hess, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 128 days.

(21) Appl. No.: 13/249,714

(22) Filed: Sep. 30, 2011

(65) Prior Publication Data

US 2013/0085509 A1   Apr. 4, 2013

(51) Int. Cl.
*A61B 19/00* (2006.01)
*A61B 17/00* (2006.01)

(52) U.S. Cl.
CPC ............. *A61B 19/2203* (2013.01); *A61B 19/22* (2013.01); *A61B 2017/00022* (2013.01); *A61B 2019/2223* (2013.01)

(58) Field of Classification Search
CPC ............... A61B 19/2203; A61B 19/22; A61B 2019/2223; A61B 2017/00022; A61B 2019/2273
USPC .................................................... 606/1, 130
See application file for complete search history.

(56) References Cited

U.S. PATENT DOCUMENTS

| | | | |
|---|---|---|---|
| 4,762,455 A | 8/1988 | Coughlan et al. | |
| 5,222,400 A * | 6/1993 | Hilton | 73/862.043 |
| 5,330,502 A | 7/1994 | Hassler et al. | |
| 5,382,885 A | 1/1995 | Salcudean et al. | |
| 5,389,849 A | 2/1995 | Asano et al. | |
| 5,697,939 A | 12/1997 | Kubota et al. | |

(Continued)

FOREIGN PATENT DOCUMENTS

| | | |
|---|---|---|
| EP | 0 364 947 A2 | 4/1990 |
| FR | 2845889 A1 | 4/2004 |

(Continued)

OTHER PUBLICATIONS

FlexDex: A Minimally Invasive Surgical Tool with Enhanced Dexterity and Intuitive Control, Awtar et al., Journal of Medical Devices, Sep. 2010, vol. 4.
Polhemus Innovation in Motion™ "Accessories Available for Polhemus Products" web page available at Polhemus web site, dated no later than Aug. 29, 2011.
Polhemus Innovation in Motion™ "Accessories" Brochure, 2004.

(Continued)

*Primary Examiner* — Katrina Stransky
(74) *Attorney, Agent, or Firm* — Mintz Levin Cohn Ferris Glovsky and Popeo, P.C.

(57) ABSTRACT

Methods and devices are provided for controlling movement of a distal end of a surgical instrument. In general, the methods and devices can allow for controlling movement of surgical tools, and in particular for causing mimicked motion between an external control unit and a surgical tool positioned within a patient's body. In one embodiment, a surgical system is provided having a master assembly including an input tool and a slave assembly including a surgical instrument. The master assembly and the slave assembly can be configured to be electronically coupled together such that movement of the master assembly can be electronically communicated to the slave assembly to cause mimicked movement of the slave assembly.

21 Claims, 6 Drawing Sheets

(56) References Cited

U.S. PATENT DOCUMENTS

| | | | |
|---|---|---|---|
| 5,702,408 A | | 12/1997 | Wales et al. |
| 5,792,135 A | | 8/1998 | Madhani et al. |
| 5,951,574 A | | 9/1999 | Stefanchik et al. |
| 6,201,984 B1 | * | 3/2001 | Funda et al. .................. 600/407 |
| 6,364,888 B1 | | 4/2002 | Niemeyer et al. |
| 6,837,883 B2 | * | 1/2005 | Moll et al. ......................... 606/1 |
| 7,398,707 B2 | | 7/2008 | Morley et al. |
| 8,521,331 B2 | | 8/2013 | Itkowitz |
| 2006/0178559 A1 | * | 8/2006 | Kumar et al. ................. 600/109 |
| 2007/0088340 A1 | | 4/2007 | Brock et al. |
| 2010/0256558 A1 | * | 10/2010 | Olson et al. ................ 604/95.01 |
| 2011/0118752 A1 | * | 5/2011 | Itkowitz et al. ............... 606/130 |
| 2012/0083768 A1 | * | 4/2012 | Skora et al. ........................ 606/1 |

FOREIGN PATENT DOCUMENTS

| | | |
|---|---|---|
| WO | WO-03/086219 A2 | 10/2003 |
| WO | WO-2009126955 A2 | 10/2009 |

OTHER PUBLICATIONS

Polhemus Innovation in Motion™ "PATRIOT DB" Brochure, 2010.
Polhemus Innovation in Motion™ "PATRIOT" Brochure, 2008.
Polhemus Innovation in Motion™ "Polhemus Motion Tracking Technical Comparisons—Tracking Performance" white paper available at Polhemus web site, dated no later than Aug. 29, 2011.
Polhemus Innovation in Motion™ "Polhemus: PATRIOT—Affordable and Accurate Motion Tracking" web page available at Polhemus web site, dated no later than Aug. 29, 2011.
Robot Technology, vol. 3A: Teleoperations and Robotics: Evolution and Development, pp. 67-93, 1986.
U.S. Appl. No. 12/971,434, filed Dec. 17, 2010 entitled "Surgical System and Methods for Mimicked Motion".
U.S. Appl. No. 12/971,491, filed Dec. 17, 2010 entitled "Surgical System and Methods for Mimicked Motion".
International Search Report and Written Opinion for Application No. PCT/US2012/056867, issued Jan. 18, 2013. (15 pages).

* cited by examiner

METHODS AND DEVICES FOR REMOTELY CONTROLLING MOVEMENT OF SURGICAL TOOLS

FIELD

The present invention relates to remotely controlling movement of surgical tools, and in particular to causing mimicked motion between an external control unit and a surgical tool positioned within a patient's body.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Conventional MIS devices include a handle, an elongate shaft, and an end effector at the distal end for effecting tissue. Motion of the end effector is typically limited to four degrees of freedom (a degree of freedom is the direction in which the end effector can move). Furthermore, motion of the end effector reverses motion of the handle, such that the operator needs to move the handle in a direction opposite to the desired direction of movement. Shear forces on MIS instruments can also be high, leading to increased operator fatigue.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the physical space required to use robotic systems during a surgical procedure and the fixed orientation of such system's robotic controls to the end effector being controlled. Another drawback is the high expense to manufacture such robotic systems.

Accordingly, there remains a need for improved methods and devices for controlling movement of a working end of an endoscopic surgical device, and in particular to methods and devices that provide for mimicking motion between an external control and an end effector.

SUMMARY

The present invention generally provides methods and devices for remotely controlling movement of surgical tools, and in particular to causing mimicked motion between an external control unit and a surgical tool positioned within a patient's body. In one embodiment, a surgical method is provided that includes advancing an elongate shaft through a surgical access point in a tissue surface to position a distal end of the elongate shaft within a body cavity, and moving one or more master sensors disposed external to the body cavity in at least one degree of freedom to cause the distal end of the elongate shaft to mimic the movement of the one or more master sensors. The one or more master sensors are in electronic communication with the elongate shaft without a physical linkage extending between the one or more master sensors and the elongate shaft.

The one or more master can be moved in a variety of ways. In one embodiment, the one or more master sensors can be disposed on a surgical instrument, and moving the one or more master sensors can include user manipulation of the surgical instrument. In another embodiment, the one or more master sensors can be positioned on a hand of a user, e.g., on fingers of the user, and moving the one or more master sensors can include moving the hand.

In some embodiments, the method can include using a camera. The method can include positioning a camera within the body cavity to visualize the distal end of the elongate shaft within the body cavity. Moving the one or more master sensors disposed external to the body cavity in the at least one degree of freedom can also cause the camera to move within the body cavity to provide continuous visualization of the distal end of the elongate shaft within the body cavity. In another embodiment, the method can include moving one or more additional master sensors disposed external to the body cavity in at least one degree of freedom to cause the camera to mimic the movement of the one or more additional master sensors. Moving the one or more master sensors can be configured to not cause movement of the camera, and moving the one or more additional master sensors can be configured to not cause movement of the distal end of the elongate shaft.

The method can vary in any number of ways. For example, the method can include moving the one or more master sensors can cause the distal end of the elongate shaft to move in six degrees of freedom, e.g., surging, heaving, swaying, pitching, yawing, and rolling. For another example, before moving the one or more master sensors to cause the distal end of the elongate shaft to mimic the movement of the one or more master sensors, a position of the one or more master sensors can be zeroed. For yet another example, causing the distal end of the elongate shaft to mimic the movement of the one or more master sensors can include rotating the distal end of the elongate shaft about a longitudinal axis of the elongate shaft. For still another example, positioning the distal end of the elongate shaft within the body cavity can include positioning an end effector at the distal end of the elongate shaft within the body cavity. The end effector can include one of a clamp, a camera, forceps, a grasper, a dissector, a needle driver, scissors, an energy device, a stapler, a clip applier/remover, a suction tool, a suturing tool, and an irrigation tool.

In another embodiment, a surgical method is provided that includes positioning a slave assembly through a surgical access point in a tissue surface and into a body cavity such that a forward end of the slave assembly is within the body cavity, and actuating an input tool of a master assembly disposed external to the body cavity and electronically coupled to the end effector to cause mimicked movement of forward end of the slave assembly within the body cavity in three translational degrees of freedom and three rotational degrees of freedom. In some embodiments, positioning the slave assembly through the surgical access point can include advancing an elongate shaft through the tissue surface to position a distal end of the elongate shaft within the body cavity. The method can include coupling the slave assembly positioned within the body cavity through a patient's body wall with a magnetic field.

The method can have any number of variations. For example, the method can include rotating the input tool about a longitudinal axis of the master assembly to cause corresponding rotation of the forward end of the slave assembly about a longitudinal axis of the slave assembly. For another example, the method can include transferring mimicked movement of the input tool on the master assembly to the forward end of the slave assembly through a mechanical movement assembly. Transferring mimicked movement through the mechanical linkage can include transferring opening and closing of the input tool to effect substantially identical opening and closing of an end effector at the forward end of the slave assembly.

In another aspect, a surgical system is provided that includes a slave assembly and a master assembly. The slave assembly includes an elongate shaft having a distal end configured to be positioned within a body cavity and perform a surgical procedure therein, and a mechanical movement assembly coupled to a proximal end of the elongate shaft. The master assembly includes one or more master sensors configured to be in electronic communication with the mechanical movement assembly such that movement of the one or more master sensors outside of the body cavity is configured to cause the mechanical movement assembly to move such that the movement of the one or more master sensors is mimicked by the elongate shaft so as to move the distal end of the elongate shaft within the body cavity. The surgical system can also include a processor configured to analyze the movement of the one or more master sensors outside of the body cavity and to instruct the mechanical movement assembly to move based on the analysis. A detector can be configured to detect motion of the one or more master sensors relative thereto and to communicate the motion to the processor for the processor to analyze.

The mechanical movement assembly can have a variety of configurations. For example, the mechanical movement assembly can include a frame including first, second, and third rails respectively configured to provide linear movement along x, y, and z axes.

BRIEF DESCRIPTION OF DRAWINGS

This invention will be more fully understood from the following detailed description taken in conjunction with the accompanying drawings, in which.

DETAILED DESCRIPTION

Figure 1:
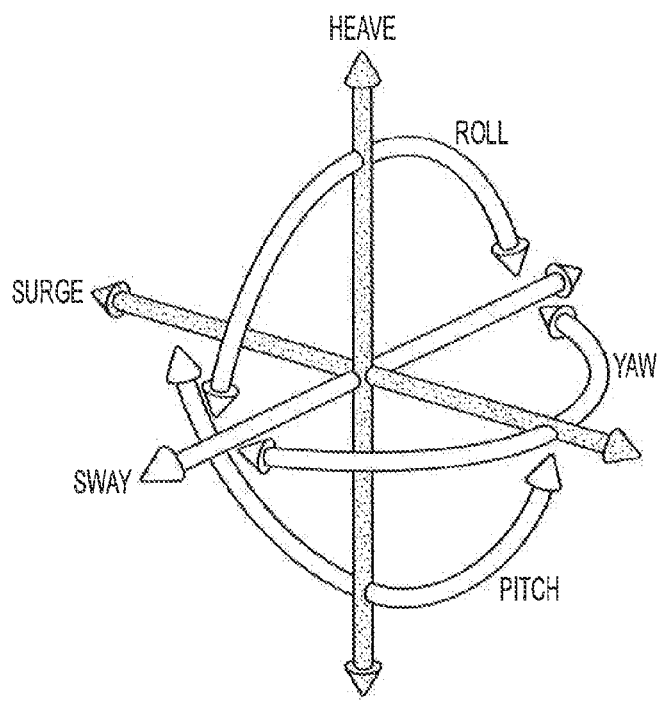
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for controlling movement of a distal end of a surgical instrument. More particularly, the provided methods and devices can cause motion of an input tool located outside a patient's body to be imparted to a distal end of a surgical instrument positioned within the patient's body during a surgical procedure. In an exemplary embodiment, a surgical system is provided having a master assembly including an input tool and a slave assembly including a surgical instrument. The master assembly and the slave assembly can be configured to be electronically coupled together such that movement of the master assembly can be electronically communicated to the slave assembly to cause mimicked movement of the slave assembly. In other words, a distal end of the slave assembly's surgical instrument can change direction or orientation in a way that is substantially identical to the movement of the master assembly's input tool, although the motion of the surgical instrument's distal end can be different in scale from the motion of the input tool. In another exemplary embodiment, the master assembly and the slave assembly can be configured to be electronically coupled together such that movement of the master assembly can be electronically communicated to the slave assembly to cause targeted, non-mimicked movement of the slave assembly, such as zooming in or zooming out of a camera.

Movement of a surgical instrument positioned within a patient's body can therefore be controlled from outside of the patient's body and can be controlled without a physical linkage extending between the one or more master sensors and the elongate shaft and/or without a user controlling movement of the surgical instrument directly contacting the surgical instrument, e.g., without the user's hands touching a handle or any other part of the surgical instrument. The user controlling movement of the surgical instrument can thus be remotely located from the patient, e.g., be located in an adjoining room, and/or need not have direct visualization of the surgical site, e.g., can indirectly view the surgical site via video. The provided methods and devices can therefore reduce crowding of surgical instruments and/or medical personnel around a patient, and/or can give the user more space in which to move when controlling movement of the surgical instrument. The provided methods and devices can also allow the user to control movement of a surgical instrument from a "backwards" position, e.g., with the user on an opposite side of a patient from which the instrument is positioned. The user can therefore control instruments positioned on multiple sides of a patient, which can help prevent the user from needing to awkwardly lean over the patient to access various instruments.

The surgical system can also include a mechanical frame. The mechanical frame can be configured to be electronically coupled to the master assembly and to be mechanically coupled to the surgical instrument such that the master assembly's movements can be electronically communicated to the mechanical frame and then be mechanically translated to the surgical instrument such that the master assembly can cause the mechanical frame to move without any physical linkage between the two, e.g., without the master assembly providing mechanical input to the mechanical frame. In addition, the mechanical frame can provide a number of additional degrees of freedom for ease of movement of the surgical system around the patient and/or the operating room.

TERMINOLOGY

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, "heave" refers to movement up and down, and "sway: refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

In general, and unless otherwise indicated, the frame of reference for rotational movement will be that of the surgical system itself. Each of the rotation axes are perpendicular to each other and remain fixed relative to the surgical system, i.e., move with the surgical system, so that the surgical system always has a pitch, roll, and yaw axis about which the system pitches, rolls, and yaws respectively. The rotational frame of reference may or may not be aligned with the translational frame of reference noted below.

In general, and unless otherwise indicated, the frame of reference for translational movement will be relative to a fixed portion of the mechanical frame to which the surgical instrument is coupled. The mechanical frame can be generally mounted or affixed to a stationary object such as a hospital bed, an operating table, the floor, the ceiling, an operating room wall, etc. Translational movement of the surgical system, as well as that of the movable portion of the mechanical frame, will be relative to this fixed portion and thus generally relative to the bed, table, floor, ceiling, wall, etc. When translational movement relative to one of the axes in this reference frame is described, it will be referred to as movement along the x, y, or z axis. When the translational movement terms are used, i.e., heave, sway, surge, they will generally refer to movement of the surgical system in that particular direction (up/down, right/left, forward/backward) relative to the translational reference frame. Such movement, however, will not necessarily be along one of the x, y, or z axes.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for the end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" will be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown or described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any of these exemplary end effectors can be utilized with the surgical system described herein. Further, an exemplary end effector is manipulated by an input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

As noted briefly above, the slave assembly of the surgical system can be positioned inside a patient's body cavity through an access point in a tissue surface for minimally invasive surgical procedures. Typically, cannulas are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave assembly, e.g., a surgical instrument, enters a body cavity through a tissue surface, whether through a cannula in a minimally invasive procedure or through an incision in an open procedure.

Surgical System

Figure 2:
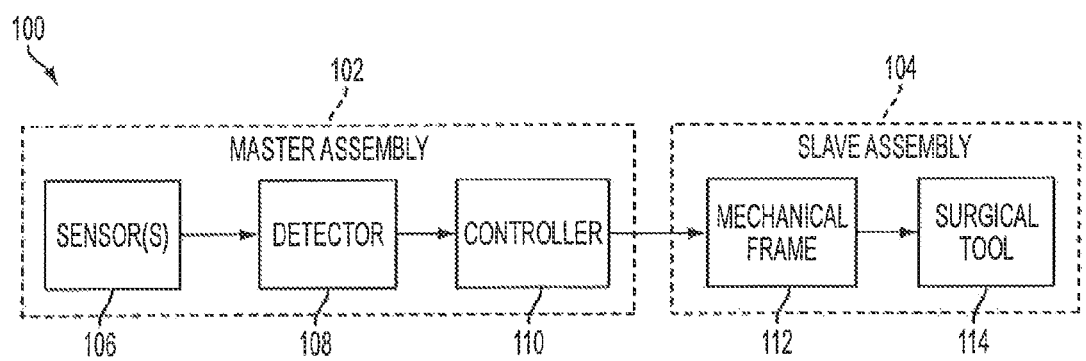
FIG. 2 is a schematic representation of one embodiment of a surgical system including a master assembly and a slave assembly.

One exemplary embodiment of a surgical system 100 configured to externally and remotely control a surgical instrument is schematically illustrated in FIG. 2. In the illustrated embodiment, the surgical system 100 includes two main components, a master assembly 102 and a slave assembly 104. The master assembly 102 can be configured for inputting user directed movement to the system 100, and the slave assembly 104 can be configured for outputting movement received from the master assembly 102. The master assembly 102 can include one or more sensors 106, a detector 108, and a controller 110. The sensors 106 can be configured to be in electronic communication with the detector 108, and the detector 108 can be configured to be in electronic communication with the controller 110. The detector 108 can be configured to emit an electromagnetic field. The sensors 106 can be configured to move relative to the detector 108 and to sense the electromagnetic field emitted by the detector 108. The detector 108 can also be configured to determine a position of each of the one or more sensors 106 relative to the detector 108 and to transmit the determined positions to the controller 110. The controller 110 can be configured to analyze the movement of the sensors 106 based on the determined positions received from the detector 108 and to transmit instructions to the slave assembly 104 based on the analyzed movement. As discussed further below, the transmitted instructions can direct mechanical movement of the slave assembly 104. An exemplary master assembly 102 is the PATRIOT™ system available from Polhemus of Colchester, Vt.

The slave assembly 104 can include a mechanical movement assembly or mechanical frame 112 and a surgical tool 114 configured to couple to the mechanical frame 112. The surgical tool 114 can be nonremovably coupled to the frame 112, or the surgical tool can be configured to be removably and replaceably coupled to the frame 112. Optionally, the frame 112 can be provided as a kit including multiple surgical tools 114, same or different from one another, with each of the tools 114 being configured to removably and replaceably couple to the frame 112. In this way, the same frame 112 can be used with a variety of tools throughout a surgical procedure and can be reused in different surgical procedures. The frame 112 can be configured to receive the instructions transmitted from the controller 110 and to mechanically move the surgical tool 114 based on the received instructions, and hence based on the movement of the sensors 106. The frame 112 can also be configured to maintain the relative orientation of the surgical tool 114 in a fixed position with respect to a surgical site and to the frame 112 until the frame 112 receives subsequent instructions from the controller 110. As discussed further below, the controller 110 can be configured to transmit a series of instructions to the frame 112 to allow the surgical tool 114 to be selectively moved to a variety of selected, different positions relative to the surgical site throughout a surgical procedure. In other words, the surgical tool 114 can be electronically controlled to simulate traditional manual, e.g., hand-held, control of the tool 114.

As will be appreciated by a person skilled in the art, electronic communication between various components of the system 100 can be wired or wireless. A person skilled in the art will also appreciate that all electronic communication in the system 100 can be wired, all electronic communication in the system 100 can be wireless, or some portions of the system 100 can be in wired communication and other portions of the system 100 can be in wireless communication.

Figure 3:
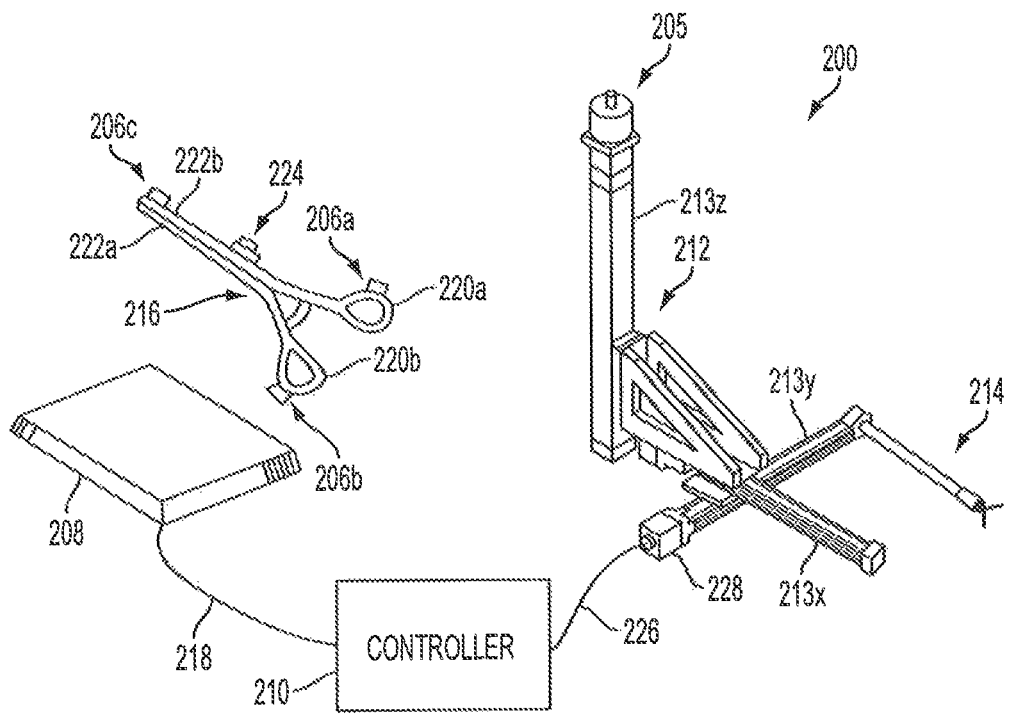
FIG. 3 is a perspective view of one embodiment of a surgical system including a master assembly and a slave assembly.

FIG. 3 illustrates an exemplary embodiment of a surgical system 200 including a master assembly and a slave assembly. The master assembly can generally include an input tool 216, sensors 206a, 206b, 206c configured to couple to the input tool 216, a detector 208 configured to be in electronic communication with the sensors 206a, 206b, 206c, and a controller 210 configured to be in electronic communication with the detector 208. The slave assembly can generally include a mechanical movement assembly or mechanical frame 212 configured to be in electronic communication with the controller 210 and a surgical tool 214 configured to couple to the frame 212.

The input tool 216 can have a variety of configurations. The input tool 216 in the illustrated embodiment includes a clamp, but the input tool 216 can include any surgical instrument configured to be manipulated by hand, e.g., a camera, forceps, a grasper, a dissector, a needle driver, scissors, a stapler, a clip applier/remover, a suction tool, a suturing tool, an energy device (e.g., an electrocautery hook, a monopolar or bipolar electrocautery tool, a harmonic tool, etc.), an irrigation tool, etc. The input tool can instead include a simulation of any such surgical tool, e.g., be a lightweight and/or less expensive reproduction such as a plastic version of a titanium device. The illustrated input tool 216 includes a proximal handle portion including first and second finger loops 220a, 220b and a distal portion including first and second clamping blades or paddles 222a, 222b. As will be appreciated by a person skilled in the art, user manipulation of the finger loops 220a, 220b away from and toward one another respectively causes the blades 222a, 222b to move toward and away from one another to facilitate clamping and release of material such as body tissue and gauze.

In the illustrated embodiment, three sensors 206a, 206b, 206c are coupled to the input tool 216, but any number of sensors can be coupled to the input tool 216. Generally, the greater the number of sensors coupled to an input tool, the more particularly a relative position of the input tool can be determined, as discussed further below. The sensors 206a, 206b, 206c can be configured to couple to the input tool 216 in any number of ways, same or different from any of the other sensors 206a, 206b, 206c coupled to the tool 216, e.g., soldering, adhesive such as glue or cement, snap fit, elastic band, etc. The illustrated sensors 206a, 206b, 206c are nonremovably coupled to the input tool 216, but in some embodiments, sensors can be removably and replaceably coupled to an input tool. In an exemplary embodiment, at least one sensor can be coupled to the tool 216 at a proximal end of the tool 216, and at least one sensor can be coupled to the tool 216 at a distal end of the tool 216. Having at least one sensor at each of the proximal and distal ends of the tool 216 can help provide sensed data regarding a substantial portion of a longitudinal length of the tool 216. In the illustrated embodiment, first and second sensors 206a, 206b are respectively coupled to the first and second finger loops 220a, 220b, and a third sensor 206c is coupled to the first blade 222a at a distal end of the blade 222a.

The sensors 206a, 206b, 206c can have a variety of configurations. Generally, each of the sensors 206a, 206b, 206c can be configured to receive and respond to a stimulus. In an exemplary embodiment, each of the sensors 206a, 206b, 206c can be configured to receive and respond to an electromagnetic field provided by the detector 208, such as by each of the sensors 206a, 206b, 206c including a magnet, a control board, and an energy source. One embodiment of an electromagnetic sensor that can be used for each of the sensors 206a, 206b, 206c is a PATRIOT™ sensor available from Polhemus of Colchester, Vt. In other exemplary embodiments, one or more sensors configured to coupled to an input tool can be configured as a vision tracker, a laser scanner, an accelerometer such as a micro electro-mechanical system (MEMS) accelerometer, and an ultrasonic sensor.

The sensors 206a, 206b, 206c of FIG. 3 are each configured to be in wireless electronic communication with the detector 208, which can allow the input tool 216 to lack any physical linkage to the detector 208, the controller 210, and the slave assembly. However, as mentioned above, any one or more of the sensors 206a, 206b, 206c can be configured to be in wired electronic communication with the detector 208. Similarly, the detector 208 can be configured to be in wired electronic communication with the controller 210 via a wire 218, e.g., a power and data cord, as in the illustrated embodiment, or the detector 208 can be configured to be in wireless electronic communication with the controller 210. Wireless communication between the controller 210 and the slave assembly can, regardless of whether the sensors 206a, 206b, 206c are wired to the detector 208 and whether the detector 208 is wired to the controller 210, can allow the master assembly to be coupled to the slave assembly without any physical linkage therebetween. Similarly, wired communication between any one or more of the sensors 206a, 206b, 206c, the detector 208, the controller 216 and wired communication The detector 208 can also have a variety of configurations. Generally, the detector 208 can be configured to emit a stimulus that can be received and responded to by the sensors 206a, 206b, 206c and to receive the response from the sensors 206a, 206b, 206c, e.g., to detect measurements sensed by the sensors 206a, 206b, 206c. In an exemplary embodiment, the detector 208 can be configured to emit an electromagnetic field which the sensors 206a, 206b, 206c can be configured to receive and respond to. The detector 208 can be configured to emit an electromagnetic field, or another stimulus, in any number of ways, as will be appreciated by a person skilled in the art, such as by including one or more electromagnetic coils that can be turned "on" when the detector 208 is supplied with electrical power. The detector 208 can be configured to emit the electromagnetic field within a certain range, e.g., up to about five feet, to help reduce interference of the electromagnetic field with, e.g., other electronic instruments. One embodiment of an electromagnetic source that can be used as the detector 208 is a PATRIOT™ source available from Polhemus of Colchester, Vt.

With the detector 208 emitting an electromagnetic field, one or more of the sensors 206a, 206b, 206c can be configured to move relative to the detector 208, e.g., to move within the electromagnetic field. The detector 208 can be configured to detect the sensors' motion and transmit the detected motion to the controller 210. The detector 208 can be configured to simultaneously detect the relative motion of more or less than the three sensors 206a, 206b, 206c of the illustrated embodiment, e.g., to detect the relative motion of up to sixteen sensors. In detecting the sensors' motion relative to the detector 208, the detector 208 can be configured to detect up to six degrees of freedom for each of the sensors 206a, 206b, 206c, e.g., three degrees of translational movement along the x, y, and z axes and three degrees of rotational movement about the x, y, and z axes. The detector 208 can be configured to transmit this detected motion to the controller 210 for analysis and for communication to the slave assembly.

The slave assembly can include a zero or reset feature configured to set an initial or "zero" position of the sensors 206a, 206b, 206c relative to the detector 208. The detector 208 can be configured to detect the relative positions of the sensors 206a, 206b, 206c with respect to the detector 208 when the zero or reset feature is actuated, and set the detected positions as the initial position of the sensors 206a, 206b, 206c. The detector 208 and/or the controller 210 can use the initial position in determining movement of the sensors 206a, 206b, 206c, e.g., in determining movement along and/or about each of the x, y, and z axes from the "zero" position, to be transmitted to the slave assembly for corresponding movement of the surgical tool 214, as discussed further below. In this way, a user manipulating the input tool 216 having the sensors 206a, 206b, 206c coupled thereto can freely move the tool 216 without movement of the sensors 206a, 206b, 206c being detected by the detector 208, and therefore without causing any movement of the slave assembly, as discussed further below, until the user is ready to cause such movement.

The zero or reset feature can have a variety of configurations, such as a depressible button 224 as shown in FIG. 3, a switch, a dial, etc. The zero or reset feature can be coupled to the input tool 216 as shown in the illustrated embodiment, e.g., by soldering, adhesive such as glue or cement, snap fit, elastic band, etc., or the zero or reset feature can be separate from the input tool 216, such as by being coupled to the detector 208 and/or another element in the system 200, e.g., a computer in communication with the controller 210.

The zero or reset feature can be configured to alternately engage and disengage the sensors 206a, 206b, 206c such that the master assembly can selectively, e.g., at the discretion of medical personnel performing a surgical procedure, cause movement of the slave assembly. A first actuation of the feature, e.g., a first press of the button 224, can engage the sensors 206a, 206b, 206c and set an initial position thereof relative to the detector 208 such that movement of the sensors 206a, 206b, 206c relative to the detector 208 can cause movement of the slave assembly, and a second, subsequent actuation of the feature, e.g., a second, subsequent press of the button 224, can disengage the sensors 206a, 206b, 206c such that movement of the sensors 206a, 206b, 206c relative to the detector 208 does not cause movement of the slave assembly. Subsequent actuations of the zero or reset feature can alternately cause such engagement and disengagement with odd-numbered actuations engaging the sensors 206a, 206b, 206c and even-numbered actuations disengaging the sensors 206a, 206b, 206c. Providing selective and engagement and disengagement of the sensors 206a, 206b, 206c can help prevent fatigue of a user manipulating the input tool by allowing the user to periodically relax his or her hand and/or relocate his or her hand relative to the detector 208 without the sensors 206a, 206b, 206c causing movement of the slave assembly. Providing selective engagement and disengagement of the sensors 206a, 206b, 206c can also allow for the slave assembly to be locked in a fixed position relative to a surgical site when in use during a surgical procedure. With the sensors 206a, 206b, 206c engaged, the slave assembly can be moved via instructions from the master assembly as discussed herein. Then, upon disengagement of the sensors 206a, 206b, 206c, the master assembly can be effectively prevented from causing movement of the slave assembly such that the slave assembly can remain in a fixed position until the sensors 206a, 206b, 206c are reengaged and moved and/or until the slave assembly is moved manually by hand.

Figure 4:
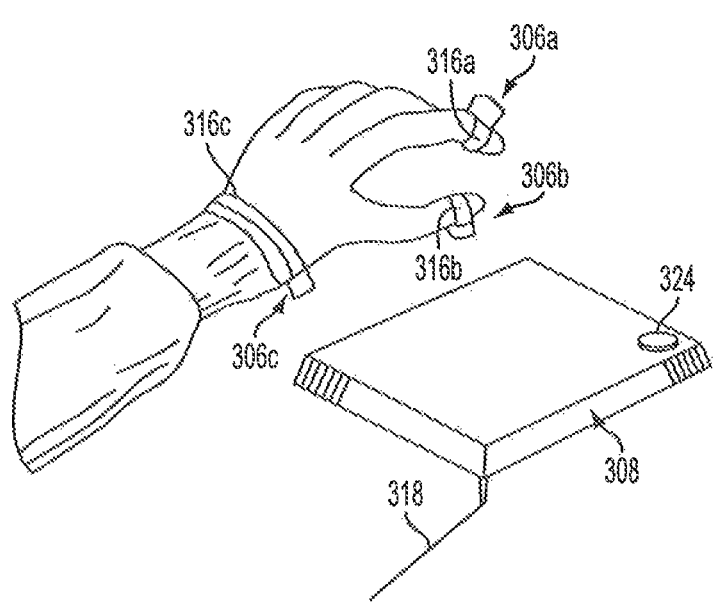
FIG. 4 is a perspective view of one embodiment of an input tool and a detector of a master assembly.

Another embodiment of an input tool includes a wearable input tool. An exemplary embodiment of a wearable input tool is illustrated in FIG. 4. In this illustrated embodiment, the input tool comprises a plurality of wearable bands 316a, 316b, 316c each having a sensor 306a, 306b, 306c coupled thereto. Although multiple bands 316a, 316b, 316c and multiple sensors 306a, 306b, 306c are shown in this embodiment, the slave assembly can include only one sensor and/or only one band. Similarly, although each of the illustrated bands 316a, 316b, 316c has a single sensor coupled thereto, any one or more of the bands 316a, 316b, 316c can have a plurality of sensors coupled thereto. Similar to that discussed above regarding FIG. 3, the sensors 306a, 306b, 306c can be configured to be in electronic communication with a detector 308, which can be configured to detect motion of the sensors 306a, 306b, 306c relative thereto. In the embodiment shown in FIG. 4, the detector 308 includes a depressible "zero" button 324 and includes a wire 318 configured to facilitate communication between the detector 308 and a controller.

The bands 316a, 316b, 316c can have a variety of configurations. Generally, each of the bands 316a, 316b, 316c can be configured to be worn on a user, e.g., clipped to clothing, a surgical mask, or glasses, worn on a finger like a ring similar to the bands 316a, 316b, worn on a wrist like a bracelet similar to the band 316c, worn on an ankle like an anklet, worn on a head like a headband, etc. In an exemplary embodiment, the bands 316a, 316b, 316c can be configured to snugly or securely fit a user such that, when worn, the bands 316a, 316b, 316c cannot move relative to user absent deliberate movement by the user, e.g., the wrist band 316c being prevented from freely sliding up and/or down the user's arm. The bands 316a, 316b, 316c can be configured to snugly or securely fit the user in a variety of ways, such as by being self-adjusting, e.g., with elastic, or by being user-adjustable, e.g., with Velcro® straps. Although the illustrated embodiment includes three bands 316a, 316b, 316c, the master assembly can include any number of wearable bands wearable in any one or more ways. Also, although the bands 316a, 316b, 316c in the illustrated embodiment are wearable on hand with two finger bands 316a, 316b and one wrist band 316c, similar to the positioning of the sensors 206a, 206b, 206c of the clamp of FIG. 3, the input tool's bands can be worn by a user in any one or more ways, e.g., all on a hand, one or more bands on a hand and one or more on an ankle, one band on each wrist, etc.

Another exemplary embodiment of a wearable input tool is a glove. The glove can be similar to the bands 316a, 316b, 316c of FIG. 4 except that instead of the sensors being positioned on bands that can be selectively worn on various portions of a hand, the sensors can be positioned on various portions of the glove, e.g., a sensor to be worn on a thumb, a sensor to be worn on an index finger, and a sensor to be worn on a wrist. The glove's sensors can be nonremovably fixed to the glove, such as being sewn thereto or fixed thereto with adhesive. Alternatively, the glove's sensors can be removably and replaceably attachable to the glove, such as with Velcro® or snaps. If the sensors are removably and replaceably attachable to the glove, the glove can be configured to receive the sensors at predetermined locations, e.g., each of the glove's fingertips can include a piece of Velcro®, or at any location thereon, e.g., the glove's entire outer surface is Velcro®. Any number of the glove's sensors can be nonremovable, and any number can be removable and replaceable. A system can be provided with a plurality of gloves in different sizes to help ensure a snug or secure fit with a variety of users.

Another embodiment of an input tool includes a pointing device having one or more sensors coupled thereto. A pointing device can be configured to transmit sensed data directly to a controller, e.g., a detector need not be included in a system in which the input tool includes a pointing device. Non-limiting examples of a pointing device include a hand-controlled or foot-controlled mouse, a joystick, a rollerball or trackball, a touchpad or touchscreen, a stylus, and a steering wheel.

Figure 5:
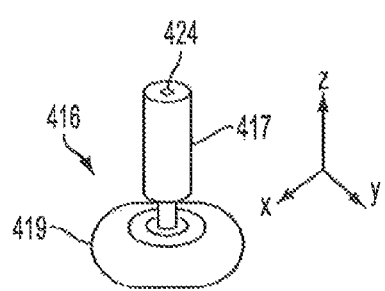
FIG. 5 is a perspective view of one embodiment of a joystick configured to be an input tool in a master assembly.

FIG. 5 illustrates an exemplary embodiment of a pointing device as a joystick 416 including at least one sensor located within the joystick 416 and therefore not visible in FIG. 5. Although the joystick 416 in the illustrated embodiment is wireless, the joystick 416 can be wired. In some embodiments, the joystick 416 can be isometric such that varying a force used to move the joystick's stick 417 can control the sensors without the stick 417 appreciably moving. As in the illustrated embodiment, the joystick 416 can be isotonic in which the stick 417 is configured to be freely movable in the x, y, and z directions. To model movement in the z direction, the stick 417 can be rotatable about a longitudinal axis thereof, or the stick 417 can be movable up and down such that the stick 417 moves into and out of a base 419 of the joystick. In some embodiments, the joystick can be configured to be freely movable in less than all three of the x, y, and z directions, such as only being movable in the x and y directions. The joystick 416 can include a "zero" button, such as on a terminal end of the stick 417 as in the illustrated embodiment.

Figure 6:
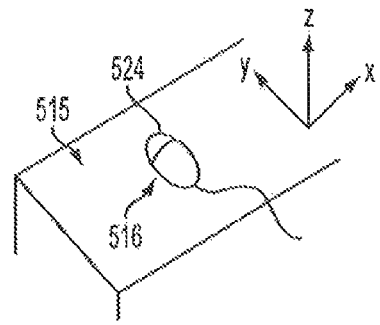
FIG. 6 is a perspective view of one embodiment of a mouse configured to be an input tool in a master assembly.

FIG. 6 illustrates another exemplary embodiment of a pointing device as a hand mouse 516 including at least one sensor located within the mouse 516 and therefore not visible in FIG. 6. The mouse 516 can include a "zero" button 524, as in the illustrated embodiment. Although the mouse 516 in the illustrated embodiment only includes one feature, the button 524, in some embodiments, the mouse 516 can include additional or alternate features, such as a scroll wheel, multiple buttons each configured for different functions, etc. A mouse's scroll wheel can, for non-limiting example, be configured to model movement in the z direction, with traditional movement of the mouse 516 in a flat plane, e.g., on a tabletop 515, being configured to model movement in the x and y directions. Also, although the mouse 516 in the illustrated embodiment is wired, the mouse 516 can be wireless.

Referring again to FIG. 3, the controller 210 can also have a variety of configurations. In an exemplary embodiment, the controller 210 can include a processor, a microcontroller, a central processing unit (CPU), etc. configured to analyze data and transmit instructions. As will be appreciated by a person skilled in the art, the controller 210 can be included as part of processing device such as a computer, server, tablet, telephone, etc., which can have a graphical user interface (GUI).

The GUI can be configured to display information such as data received from the detector 208, the analyzed data, the transmitted instructions, video of the surgical tool 214, whether the sensors 206a, 206b, 206c are engaged or disengaged, etc.

The controller 210 is shown in FIG. 3 as a standalone element positioned between the detector 208 and the frame 212, but the controller 210 can be included in the detector 208 or included in the frame 212. The controller 210 is configured to be in wired electronic communication with the frame 212 via a wire 226, e.g., a power and data cord, in the illustrated embodiment, but the controller 210 can be configured to be in wireless electronic communication with the frame 212.

Generally, the controller 210 can be configured to receive the detected motion from the detector 208 and analyze the movement of the sensors 206a, 206b, 206c based on the detected motion. Based on the analysis, the controller 208 can transmit instructions to the slave assembly to move the surgical tool 214. Generally, the controller's transmitted instructions can cause the surgical tool 214 to mimic the movement of the sensors 206a, 206b, 206c. In an exemplary embodiment, the controller 210 can be configured to analyze data received from the detector 208, and/or directly from the input tool 216, to determine movement of the sensors 206a, 206b, 206c from a first position relative to the detector 208 to a second, subsequent position relative to the detector 208 to determine how the surgical tool 214 is being directed to move. The controller 210 can be configured to continuously analyze received data such that the surgical tool 214 can be continuously directed to move substantially in real time with the movement of the input tool 216. Because each of the sensors 206a, 206b, 206c in this illustrated embodiment can be configured to move in up to six degrees of freedom, e.g., heave, sway, surge, roll, yaw, and pitch, relative to the detector 208, the controller 208 can be configured to analyze movement in a total number of degrees of freedom equal to six times a number of sensors, which in this illustrated embodiment is eighteen. The surgical tool 214 can therefore be directed to move in a total number of degrees of freedom equal to or less than six times a number of sensors included in the system 200.

In embodiments in which the slave surgical tool includes a viewing element, the controller 208 can be configured to transmit instructions causing the viewing element to zoom in or out based on particular spatial motions of the master assembly's sensor(s). For non-limiting example, if the controller 208 determines that the sensor(s) were moved in a particular spatial motion such as a wide circular motion, the controller 208 can transmit instructions to the slave assembly to zoom out the viewing element, whereas if the controller 208 determines that the sensor(s) were moved in a particular spatial motion such as a tight circular motion, the controller 208 can transmit instructions to the slave assembly to zoom in the viewing element. In such an embodiment, actuation of the zero feature can be configured to cause the viewing element to adjust to a predetermined zoom level, e.g., a 100% zoom level.

The controller 208 can be configured to transmit movement instructions to the slave assembly that maintain a 1:1 ratio between movement of the input tool 216 and movement of the surgical tool 214 can be maintained regardless of a location of the surgical tool 214 relative to a patient, e.g., regardless of a depth of penetration of the surgical tool 214 within the patient. For non-limiting example, if the input tool 216 moves 10 mm in the x direction such that each of the sensors 206a, 206b, 206c moves 10 mm in the x direction, then the surgical tool 214 can be directed to move 10 mm in the x direction. In some embodiments, however, the controller 208 can be configured to provide instructions to the slave assembly that cause scaled motion between the input tool 216 and the surgical tool 214. The controller 208 can be configured to scale down movement of the input tool 216 so that the surgical tool 214 moves in the same degrees of freedom as the input tool 216 but to a lesser degree than the input tool 216. Similarly, the controller 208 can be configured to scale up movement of the input tool 216 so that the surgical tool 214 moves in the same degrees of freedom as the input tool 216 but to a greater degree than the input tool 216. For non-limiting example, the controller 208 can be configured to process received data so the ratio of input to output is, e.g., 2:1, such that the size of motion inputted into the system 200 through the input tool 216 will result in motion scaled by half in the slave assembly. Scaling down movement of the input tool 216 to the surgical tool 214 can allow for more precise positioning of the surgical tool 214, which can help reduce chances of the surgical tool 214 damaging body tissue and/or interfering with any nearby tools positioned within a patient. A person skilled in the art will appreciate the variations and possibilities of scaled motion between the master assembly and the slave assembly.

In some embodiments, in addition to the controller 208 being configured to transmit instructions to the slave assembly to cause the surgical tool 214 to move based on movement of the sensors 206a, 206b, 206c, the controller 208 can be configured to transmit one or more additional instructions to the slave assembly based on that same movement of the sensors 206a, 206b, 206c. The additional transmitted instructions can cause one or more additional surgical tools included in the slave assembly to mimic the movement of the input tool 216. In other words, movement of the input tool 216 can be configured to cause movement of two or more surgical tools included in the slave assembly. In this way, movement of multiple surgical tools can occur substantially simultaneously and can be coordinated, which can reduce interference between the surgical tools, can improve a surgical procedure's efficiency, and can reduce a number of hands needed to control surgical tools in simultaneous use during a surgical procedure. The controller 208 can be configured to simultaneously or sequentially transmit multiple instructions. A person skilled in the art will appreciate that the controller 208 can be configured to scale none of the instructions it transmits, to scale all of the instructions it transmits using same or different scales for each of the instructions, or to scale some instructions but not other instructions.

In an exemplary embodiment in which the controller 208 transmits instructions for movement of two or more surgical instruments, the controller 208 can be configured to transmit instructions to the frame 212 to cause movement of the surgical tool 214 and to transmit instructions to N mechanical frames (not shown in FIG. 3) to cause movement of N surgical tools, where N is a positive integer equaling one or more. Alternatively, the surgical tool 214 and N additional surgical tool(s) can be coupled to the same mechanical frame 212.

In one exemplary embodiment, the controller 208 can be configured to transmit instructions to cause the surgical tool 214 to move based on analyzed movement of the sensors 206a, 206b, 206c and to transmit instructions to cause a viewing element, e.g., a camera, a lens, etc., visualizing a distal end of the surgical tool 214 to move based on analyzed movement of the sensors 206a, 206b, 206c. In this way, movement of the viewing element can be coordinated with the surgical tool 214 so as to help maintain visualization of the distal end of the surgical tool 214 during and/or after movement of the surgical tool 214 as instructed by the controller 208. The movement of the viewing element can, e.g., mimic the movement of the surgical tool 214 and/or include zooming in and/or zooming out. In some embodiments, the controller 208 can be configured to analyze patterns in the sensors' movement based on predetermined or preprogrammed surgical tool movement common in various surgical procedures. If, based on the movement of the sensors 206a, 206b, 206c during the surgical procedure, the controller 208 determines that a particular orientation and/or zoom level of the viewing element would be desirable, then the controller 208 can transmit instructions to cause the viewing element to move to the particular orientation and/or to zoom to the particular zoom level. The controller 208 can additionally or alternatively be configured to base its transmitted instructions on an amount of time lapsed during a surgical procedure. For non-limiting example, if sixty minutes have passed since a surgical procedure began, then the controller 208 can anticipate that a particular aspect of the procedure is about to be performed and move the viewing element accordingly. The system 200 can include an override feature to cancel or delay the controller's determined viewing element movement. The controller 208 can be configured to learn over time by storing movements of the sensors 206a, 206, 206c during different surgical procedures and using the stored real-world movements to help determine future movement instructions. Further, controller 208 can be configured to analyze stored information for only the same type of surgical procedure being performed and/or to analyze stored information for only the particular surgeon performing the surgical procedure. Such targeted analysis of stored information can help the controller 208 better determine desirable and/or anticipated movements of a slave tool.

In another exemplary embodiment, the controller 208 can be configured to transmit instructions to cause the surgical tool 214 to move based on analyzed movement of the sensors 206a, 206b, 206c and to transmit instructions to cause a suction and/or irrigation tool targeted at the surgical tool 214 to move based on analyzed movement of the sensors 206a, 206b, 206c. In this way, movement of the suction and/or irrigation tool can be coordinated with the surgical tool 214 so as to help maintain suction and/or irrigation targeted at the surgical tool 214 during and/or after movement of the surgical tool 214 as instructed by the controller 208.

As in the illustrated embodiment of FIG. 3, the controller 208 can be configured to analyze movement of all of the input tool's sensors 206a, 206b, 206c in determining instructions to transmit to the slave assembly and, if present, to one or more additional slave assemblies. In some embodiments, various ones of the input tool's sensors can be dedicated to a particular slave device such that the controller 208 only bases its instructions to cause movement of a particular slave device on a subset of a total number of the sensors. In this way, relative positioning of multiple surgical tools can be better maintained. For non-limiting example, the finger loop sensors 206a, 206b can correspond to the surgical tool 214 such that the controller 208 analyzes movement of the finger loop sensors 206a, 206b, but not the blade sensor 206c, in determining movement instructions for the surgical tool 214, and the blade sensor 206c can correspond to a second surgical tool (not shown in FIG. 3) such that the controller 208 analyzes movement of the blade sensor 206c, but not the finger loop sensors 206a, 206b, in determining movement instructions for the second surgical tool.

Figure 7:
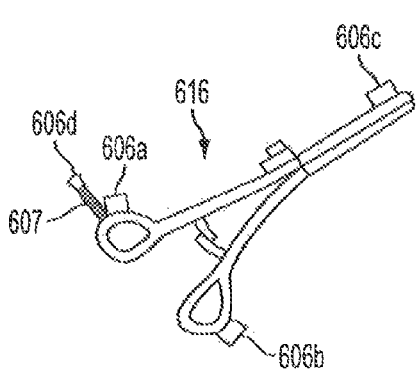
FIG. 7 is a perspective view of another embodiment of an input tool of a master assembly.

FIG. 7 illustrates an embodiment of an input tool 616 configured to control movement of multiple slave surgical tools such that the slave surgical tools can be simultaneously moved and such that one or more of the slave surgical tools can be moved independent of the other slave surgical tools. The input tool 616 is similar to the input tool 216 of FIG. 3 except that in addition to having three sensors 606a, 606b, 606c similar to the sensors 206a, 206b, 206c of FIG. 3, the input tool 616 has an additional sensor 606d coupled thereto. The additional sensor 606d can be configured to move with the other sensors 606a, 606b, 606c and configured to move relative to the other sensors 606a, 606b, 606c. In other words, the additional sensor 606d corresponding to a slave surgical tool can be configured to be actuated independent of the other sensors 606a, 606b, 606c corresponding to another slave surgical tool. In this way, the slave surgical tool and the other slave surgical tool can be configured to move in a coordinated fashion, e.g., when the tool 616 is moved so as to move all of the sensors 606a, 606b, 606c, 606d, and the slave surgical tool can be configured to move independent of the other slave surgical tool, e.g., when the additional sensor 606d is moved relative to the other sensors 606a, 606b, 606c. The input tool 616 can also allow a user to control two devices with one hand, e.g., two slave surgical tools, which can free the user's other hand for other work. The additional sensor 606d is coupled to the input tool 616 via a coiled compression spring 607 in the illustrated embodiment such that the spring 607 can be freely and selectively pushed or urged in the x, y, and/or z directions, e.g., with the user's thumb while the user is gripping the tool 616, to move the sensor 606d relative to the other sensors 606a, 606b, 606c. However, the additional sensor 606d can be coupled to the input tool 616 using any connection element, as will be appreciated by a person skilled in the art, such as by another type of spring, a bendable rubber rod, a joystick attached to the tool 616, etc. A person skilled in the art will also appreciate that while the input tool 616 includes only one independently movable sensor 606d, the input tool 616 can include any number of independently movable sensors coupled to the compression spring 607 (or other connection element) or to different compression springs (or other connection elements).

Figure 8:
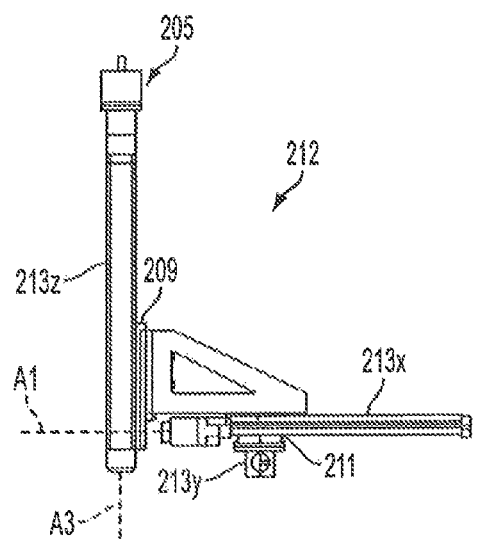
FIG. 8 is a side view of a mechanical frame of the slave assembly of FIG. 2.
Figure 9:
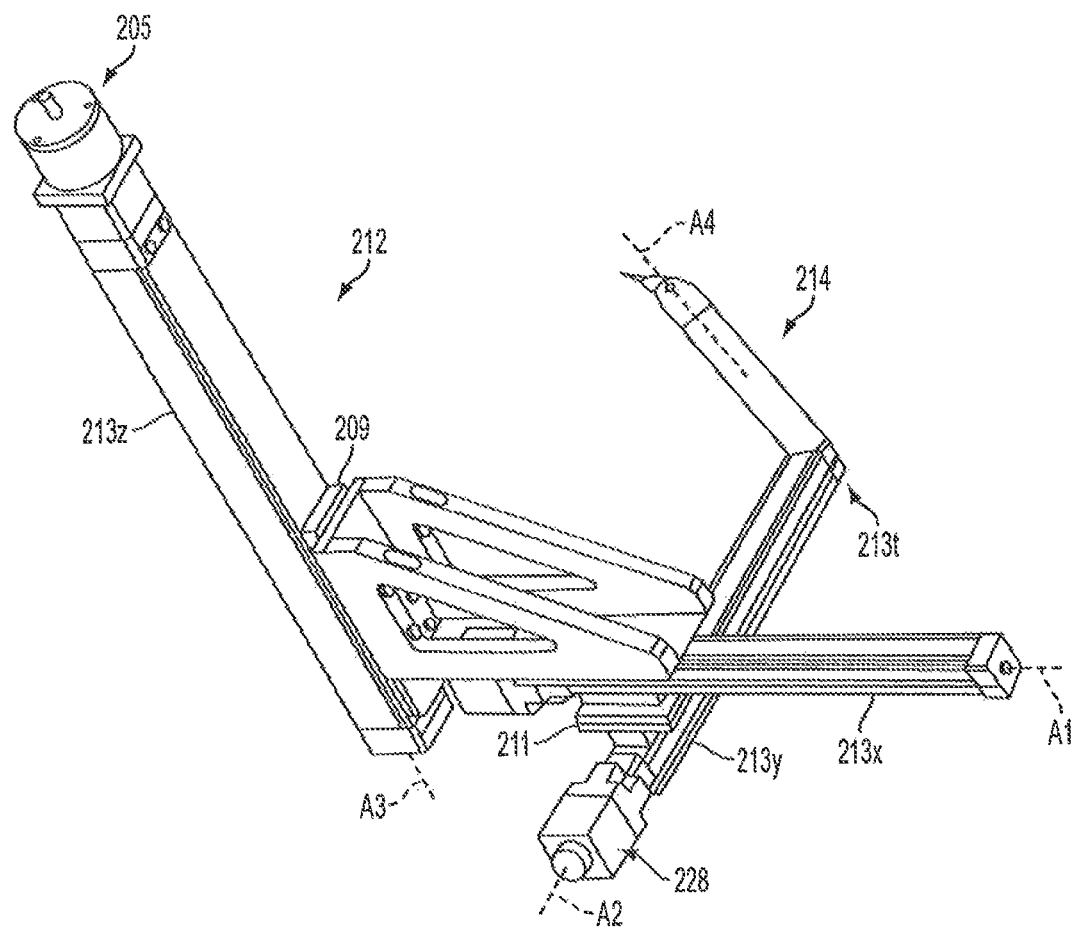
FIG. 9 is a perspective view of the mechanical frame of FIG. 8.

Referring again to FIG. 3, the mechanical frame 212 of the slave assembly can have a variety of configurations. Generally, the frame 212, which is also illustrated in FIGS. 8 and 9, can be configured to provide up to six degrees of freedom to the surgical tool 214 coupled thereto. As in the illustrated embodiment, the frame 212 can include first, second, and third rails 213x, 213y, 213z coupled together in a formation perpendicular to one another to mimic a Cartesian coordinate system and respectively correspond to x, y, and z axes A1, A2, A3. Generally, the frame 212 can allow for linear movement of the first, second, and third rails 213x, 213y, 213z, e.g., linear movement along the x, y, and z axes A1, A2, A3, to provide for movement of the surgical tool 214 in up to six degrees of freedom, e.g., The rails 213x, 213y, 213z can be coupled together in a variety of ways. As in the illustrated embodiment, the first and second rails 213x, 213y can be coupled together via a first coupler 211, and the second rail 213y can be coupled to the third rail 213z via a second coupler 209. The first and second rails 213x, 213y can be slideably coupled to the first coupler 211 such that the first rail 213x can be configured to slide along the first coupler 211 along the x axis A1 to move forward and backward relative to the second and third rails 213y, 213z. The second rail 213y can be configured to slide along the first coupler 211 along the y axis A2 to move left and right relative to the first and third rails 213x, 213z. The third rail 213z can be slideably coupled to the second coupler 209 such that the second coupler 209 can slide along the third rail 213z to jointly move the first and second rails 213x, 213y up and down along the z axis A3. Only one of the first and second rails 213x can slide along the first coupler 211 at a time, both of the first and second rails 213x can slide along the first coupler 211 at a time, and the second coupler 209 can slide along the third rail 213z at a same or different time as movement of either of the first and second rails 213x, 213y along the first coupler 211. In this way, movement of the rails 213x, 213y, 213z can accommodate instructions received from the controller 208 for simultaneous translational movement in any one or more of the x, y, and z directions and for sequential translational movement in any one or more of the x, y, and z directions.

Although the rails 213x, 213y, 213z in the illustrated embodiment are slideably coupled together via the couplers 209, 211, as referenced above, the rails 213x, 213y, 213z can be coupled together in other ways. For non-limiting example, instead of the two couplers 209, 211, the rails 213x, 213y, 213z can be coupled together via two rack and pinion mechanisms.

In the illustrated embodiment, none of the rails 213x, 213y, 213z are configured for rotation about their respective longitudinal axes. In some embodiments, however, one or more of the rails 213x, 213y, 213z can be configured for rotation about their respective longitudinal axes to provide the surgical tool 214 with up to three degrees of rotational movement, e.g., roll, pitch, and yaw. Nevertheless, in addition to the illustrated embodiment being configured to provide translational degrees of movement to the surgical tool 214 coupled to the frame 212 as discussed above, the frame 212 can be configured to provide up to three rotational degrees of freedom, e.g., roll, pitch, and yaw, to the surgical tool 214 via an attachment mechanism configured to couple the surgical tool 214 to the frame 212.

The frame 212 can be configured to couple to the surgical tool 214 in a variety of ways. As in the illustrated embodiment, a terminal end 213t of one of the rails 213x, 213y, 213z, e.g., the second rail 213y, can be configured to couple to the surgical tool 214 via an attachment mechanism such as snap fit, threaded engagement, etc. Alternatively, as mentioned above, the surgical tool 214 can be nonremovably fixed to the frame 212. Providing the surgical tool 214 at a terminal end of a rail can help prevent the surgical tool 214 from interfering with the movement of the rails 213x, 213y, 213z relative to one another. However, although the terminal end 213t of the second rail 213y is configured to couple to the surgical tool 214, any portion of the rail 213y can be configured to couple to the surgical tool 214. Although only the second rail 213y is configured to attach to the surgical tool 214 in the illustrated embodiment, any one or more of the rails 213z, 213y, 213z can be configured to attached to the surgical tool 214.

The portion of the frame 212 configured to couple to the surgical tool 214, e.g., the terminal end of the second rail 213y, can be configured to rotate in up to three degrees of freedom relative to a remainder of the frame 212. In this way, the surgical tool 214 coupled to the terminal end of the second rail 213y can be configured to rotate in up to three degrees of freedom, e.g., to rotate about one or more of the x, y, and z axes A1, A2, A3. For non-limiting example, the surgical tool 214 is shown at a position in FIG. 9 rotated about the second rail's axis A2 from the position of the surgical tool 214 shown in FIG. 3. In FIG. 3, a longitudinal axis A4 of the surgical tool 214 is substantially parallel to the first axis A1, while in FIG. 9, the tool's longitudinal axis A4 is substantially parallel to the third axis A3. The terminal end of the second rail 213y can be configured to rotate the surgical tool 214 360° about each of the axes A1, A2, A3.

The frame 212 can also be configured to couple to the controller 208 in a variety of ways. In this illustrated embodiment, the wire 226 couples the controller 208 to the frame 212 at a terminal end of the second rail 213y opposite to the terminal end which is configured to couple to the surgical tool 214. The terminal end of the second rail 213y can therefore include a frame controller 228, e.g., a processor, a microcontroller, a central processing unit (CPU), etc. configured to execute the instructions received from the controller 208. Although the terminal end of the second rail 213y is configured to couple to the controller 208 via the wire 226, any portion of the rail 213y can be configured to couple to the controller 208. Further, although only the second rail 213y is configured to attach to the wire 226 in the illustrated embodiment, any one or more of the rails 213z, 213y, 213z can be configured to be attached to the surgical tool 214. The controller 228 can transmit instructions to one or more motors (not shown) coupled to the frame 212 and configured to drive movement of the rails 213z, 213y, 213z, e.g., a dedicated linear motor for each of the rails 213z, 213y, 213z configured to drive its associated one of the rails 213z, 213y, 213z.

As mentioned above, the frame 212 can be configured to be mounted or affixed to a stationary object, which can help keep the frame 212 steady when one or more of the rails 213x, 213y, 213z and the surgical tool 214 are in motion. The frame 212 can be configured for such mounting or affixing in a variety of ways, such as by mounting a backside of the third rail 213z to a wall or by mounting a terminal end of the third rail 213z to a tabletop. As in the illustrated embodiment, the third rail 213z can be configured to be mounted to a stationary object via a plug 205 at a terminal end thereof, which can be configured to be received in a corresponding socket (not shown) formed in a ceiling, wall, etc. The plug 205 can optionally also be configured be provide electrical power to the frame 212 when plugged into the socket. Alternatively, the frame 212 can receive electrical power from a battery (not shown), the controller 208, or from another power source.

Figure 10:
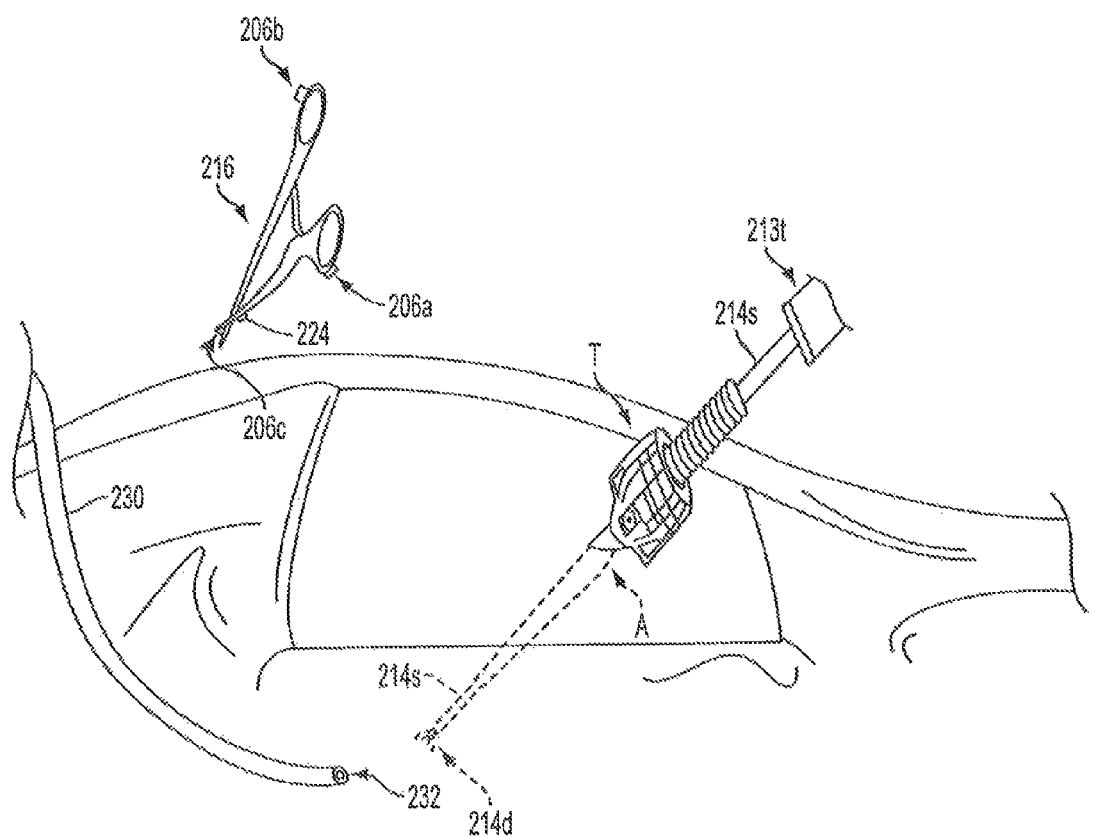
FIG. 10 is a perspective, cross-sectional, partially transparent view of one embodiment of using the surgical system of FIG. 3.
Figure 11:
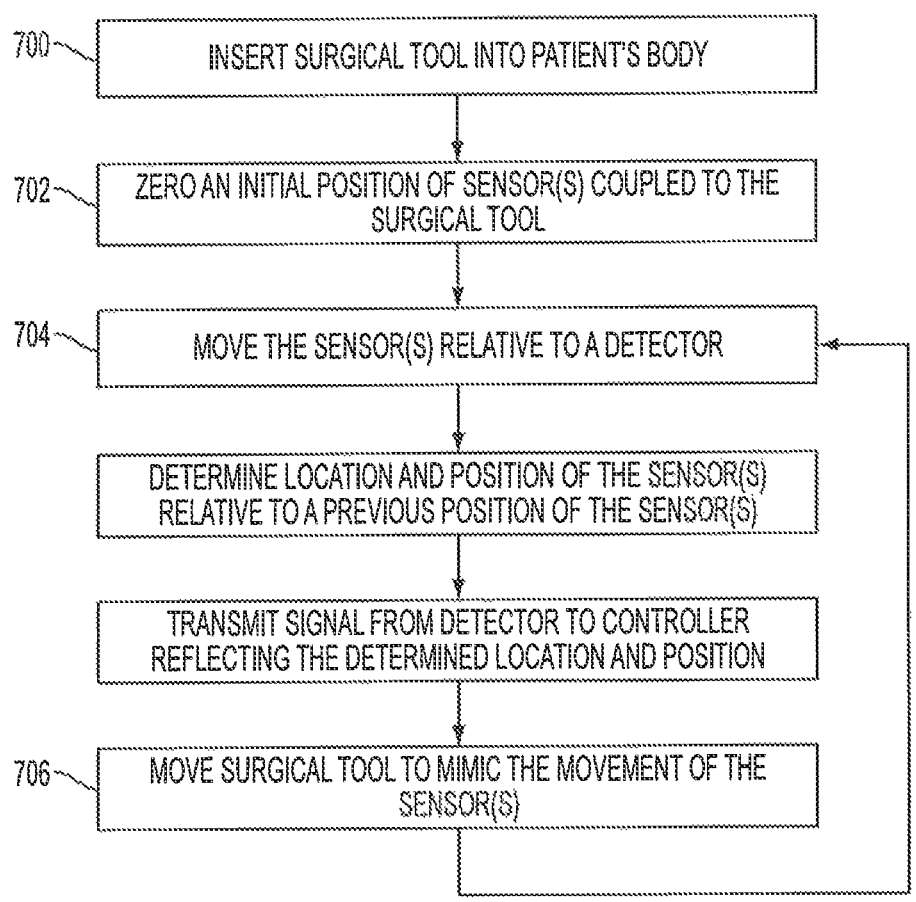
FIG. 11 is a flowchart showing one embodiment of using the surgical system of FIG. 2.

There are many methods for using the above described surgical system 200 and other embodiments of a surgical system described herein. In use, the positioning and orientation of the sensors 206a, 206b, 206c as described above can result in the transfer of mimicked motion from the input tool 216 to the surgical tool 214. As shown in an exemplary embodiment illustrated in FIGS. 10 and 11, when the surgical system 200 is in position near a patient, as shown in FIG. 10, an elongate shaft 214s of the surgical tool 214 can be inserted 700 through a surgical access point A in a tissue surface, such as a trocar T or other access cannula, so that a distal end 214d of the surgical tool 214 can be disposed within a body cavity, e.g., an abdominal cavity. Although the elongate shaft 214s is shown inserted into the body cavity through the trocar T, the elongate shaft 214s can be directly inserted into the body cavity without an access cannula, e.g., directly through an incision. Once the elongate shaft 214s is disposed through the access point A such that the tool's distal end 214d is positioned within the body cavity, the master assembly's sensors 206a, 206b, 206c coupled to the input tool 216 can be zeroed 702 by actuating the zero button 224. Movement of the master assembly, e.g., movement 704 of the sensors 206a, 206b, 206c positioned exterior to the patient as shown in FIG. 10, can then result in mimicked movement of the slave assembly as discussed above to cause movement 706 of the slave assembly as needed to perform a surgical procedure. Additionally, the slave assembly can be forcibly or manually moved, e.g., manipulated by hand, pushed or otherwise moved by one or more surgical tools, etc., before and/or after the master assembly is moved to cause movement of the slave assembly.

While disposed through the access point A, movement of the surgical tool 214 can be constrained. In particular, due the surgical tool's shaft 214 being confined in the trocar T, the surgical tool 214 can no longer heave or sway thus removing two of the translational degrees of freedom. However, the surgical tool 214 can still surge, pitch, and yaw while constrained by the access point A and thus the surgical tool 214 can have three degrees of freedom when in such a position inserted through the trocar T.

FIG. 10 also illustrates an endoscope 230 including a camera lens 232 at a distal end thereof advanced into the body cavity with the lens 232 near the distal end 214*d* of the tool 214 so as to provide visualization of the tool's distal end 214*d*, e.g., via a GUI in communication with the controller 208 (not shown in FIG. 10). The lens 232 can be configured to move as a second slave surgical tool in response to movement of one or more sensors positioned outside the patient's body, as discussed above. Although the viewing element is illustrated in this embodiment as a lens of an endoscope, as mentioned above, the viewing element can have a variety of other configurations. Also, although the endoscope 230 is shown inserted into the body cavity through a tissue incision formed in the patient, the endoscope 230 can be inserted into the patient in a variety of ways, e.g., through another trocar, transorally, etc.

Once the surgical procedure is complete, or when the tool 214 is no longer needed in the procedure, the tool's distal end 214*d* and the tool's elongate shaft 214*s* can be withdrawn from the surgical access point A. A person skilled in the art will appreciate that the above described embodiment has applications in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   advancing first and second elongate shafts through a tissue surface to position distal ends of the first and second elongate shafts within a body cavity;
   moving a first master sensor of an input tool disposed external to the body cavity in at least two degrees of freedom to cause the distal end of the first elongate shaft to mimic the movement of the first master sensor only by slidably translating the first elongate shaft along at least two of x, y, and z axes without rotational movement about the respective axes; and
   moving a second master sensor of the input tool to cause the distal end of the second elongate shaft to mimic the movement of the second master sensor, the first master sensor being in electronic communication with the first elongate shaft and the second master sensor simultaneously being in electronic communication with the second elongate shaft without a physical linkage extending between the first and second master sensors and the first and second elongate shafts.

2. The method of claim 1, wherein the input tool comprises a surgical instrument, and moving at least one of the first and second master sensors comprises user manipulation of the surgical instrument.

3. The method of claim 1, wherein at least one of the first and second master sensors are positioned on a hand of a user, and moving at least one of the first and second master sensors comprises moving the hand.

4. The method of claim 3, wherein the input tool comprises one of a glove and a plurality of wearable bands, and the first and second master sensors are mounted on fingers of the user.

5. The method of claim 1, wherein moving at least one of the first and second master sensors causes the distal end of at least one of the first and second elongate shafts to move in six degrees of freedom.

6. The method of claim 1, further comprising, before moving the first and second master sensors, zeroing a position of the first and second master sensors.

7. The method of claim 1, further comprising positioning a camera within the body cavity to visualize the distal end of at least one of the first and second elongate shafts within the body cavity;
   wherein moving at least one of the first and second master sensors disposed external to the body cavity also causes the camera to move within the body cavity to provide continuous visualization of the distal end of the at least one of the first and second elongate shafts within the body cavity.

8. The method of claim 1, further comprising positioning a camera within the body cavity to visualize the distal end of at least one of the first and second elongate shafts within the body cavity; and
   moving one or more additional master sensors disposed external to the body cavity in at least one degree of freedom to cause the camera to mimic the movement of the one or more additional master sensors;
   wherein moving the first and second master sensors does not cause movement of the camera, and moving the one or more additional master sensors does not cause movement of the distal ends of the elongate shafts.

9. The method of claim 1, further comprising moving at least one of the first and second master sensors to cause the distal end of at least one of the first and second elongate shafts to mimic the movement of the at least one of the first and second master sensors by rotating the distal end of the at least one of the first and second elongate shafts about a longitudinal axis of the at least one of the first and second elongate shafts.

10. The method of claim 1, wherein positioning the distal end of at least one of the first and second elongate shafts within the body cavity comprises positioning an end effector at the distal end of the at least one of the first and second elongate shafts within the body cavity.

11. The method of claim 10, wherein the end effector includes one of a clamp, a camera, forceps, a grasper, a dissector, a needle driver, scissors, a stapler, a clip applier/remover, a suction tool, a suturing tool, an energy device, and an irrigation tool.

12. The method of claim 1, wherein the at least two degrees of freedom includes first, second, and third degrees of freedom, and the first elongate shaft only slidably translates along all of the x, y, and z axes.

13. A surgical method, comprising:
positioning a slave assembly through a surgical access point in a tissue surface and into a body cavity such that a forward end of the slave assembly is within the body cavity; and
moving first and second sensors positioned on a proximal portion of an input tool of a master assembly toward one another so as to cause third and fourth sensors positioned on a distal portion of the input tool to move away from one another, the input tool being disposed external to the body cavity and electronically coupled to the forward end of the slave assembly to cause the forward end of the slave assembly to mimic the movement of the third and fourth sensors within the body cavity in three translational degrees of freedom and three rotational degrees of freedom, the movement in the three translational degrees of freedom being caused by translation of the forward end of the slave assembly along first, second, and third perpendicular axes such that the forward end of the slave assembly can only move in straight lines to achieve the movement in the three translational degrees of freedom.

14. The method of claim 13, further comprising rotating the input tool about a longitudinal axis of the master assembly to cause corresponding rotation of the forward end of the slave assembly about a longitudinal axis of the slave assembly.

15. The method of claim 13, wherein positioning the slave assembly through the surgical access point comprises advancing an elongate shaft through the tissue surface to position a distal end of the elongate shaft within the body cavity.

16. The method of claim 13, further comprising transferring mimicked movement of the input tool on the master assembly to the forward end of the slave assembly through a mechanical movement assembly.

17. The method of claim 16, wherein transferring mimicked movement through the mechanical movement assembly includes transferring opening and closing of the input tool to effect substantially identical opening and closing of an end effector at the forward end of the slave assembly.

18. A surgical system, comprising:
a slave assembly including an elongate shaft having a distal end configured to be positioned within a body cavity and perform a surgical procedure therein, and a mechanical movement assembly comprising first, second, and third rails respectively configured to provide linear movement of the elongate shaft along x, y, and z axes, the first, second, and third rails limiting movement of the elongate shaft to linear movement along the x, y, and z axes without rotational movement about the respective axes, and at least one of the first, second, and third rails being coupled directly to the elongate shaft; and
a master assembly including one or more master sensors configured to be in electronic communication with the mechanical movement assembly such that movement of the one or more master sensors outside of the body cavity is configured to cause the mechanical movement assembly to move such that the movement of the one or more master sensors is mimicked by the elongate shaft so as to move the distal end of the elongate shaft within the body cavity.

19. The system of claim 18, further comprising a processor configured to analyze the movement of the one or more master sensors outside of the body cavity and to instruct the mechanical movement assembly to move based on the analysis.

20. The system of claim 19, further comprising a detector configured to detect motion of the one or more master sensors relative thereto and to communicate the motion to the processor for the processor to analyze.

21. The system of claim 18, wherein the first rail is moveable along the x axis relative to the second and third rails, the second rail is moveable along the y axis relative to the first and third rails, and the third rail is moveable along the z axis relative to the first and second rails.

* * * * *